United States Patent [19]

Shorr et al.

[11] Patent Number: 5,527,775
[45] Date of Patent: Jun. 18, 1996

[54] REDUCTION OF MAMMALIAN NEOPLASMS WITH PHOSPHOLIPASE A2 ACTIVATING SUBSTANCES

[75] Inventors: Robert G. L. Shorr, Edison; Mike A. Clark, Denville, both of N.J.

[73] Assignee: Enzon, Inc., Piscataway, N.J.

[21] Appl. No.: 323,444

[22] Filed: Oct. 13, 1994

[51] Int. Cl.$^6$ .......................... A61K 38/09; A61K 38/10; A61K 38/16; A61K 38/17
[52] U.S. Cl. .................. 514/12; 514/13; 514/14; 514/15; 514/16; 514/17; 514/21
[58] Field of Search .................. 530/350, 395; 514/8, 12, 13, 14, 15, 16, 17, 21

[56] References Cited

U.S. PATENT DOCUMENTS

| | | | |
|---|---|---|---|
| 5,122,614 | 6/1992 | Zalipsky | 548/520 |
| 5,200,176 | 4/1993 | Wong et al. | 424/85.1 |
| 5,230,886 | 7/1993 | Treon et al. | 514/21 |
| 5,294,698 | 3/1994 | Bomalski et al. | 530/324 |

OTHER PUBLICATIONS

PNAS, vol. 86, issued Dec. 1989, Beyaert et al, "Lithium chloride potentiates tumor necrosis factor . . .", pp. 9494–9498.

Bomalaski, John S. et al. "Phospholipase A$_2$–Activating Protein Induces the Synthesis of IL–1 and TNF in Human Monocytes," *J. Immunol.* 154:4027–4031, 1995.

Peitsch, Manuel C. et al. "Sequence similarity of phospholipase A$_2$ activating protein and the G protein β–subunits; a new concept of effector protein activation in signal transductic?", *TIBS* 18:292–293, 1993.

Bomalaski et al., "A phospholipase A$_2$–activating protein (PLAP) stimulates human neutrophil aggregation and release of lysosomal enzymes, superoxide, and eicosanoids", *J. of Immunol.* 142(11):3957–3962 (Jun. 1, 1989).

Clark et al., "Cloning of phospholipase A$_2$–activating protein", *Proc. Natl. Acad. Sci. USA* 88:5418–5422 (Jun. 1991).

Clark et al., "Leukotriene D$_4$ treatment of bovine aortic endothelial cells and murine smooth muscle cells in culture results in an increase in phospholipase A$_2$ activity", *Biol. Chem.* 261:10713–10718 (Aug. 15, 1986).

Clark et al., "Tumour necrosis factor (cachectin) induces phospholipase A$_2$ activity and synthesis of a phospholipase A$_2$–activating protein in endothelial cells", *Biochem. J.* 250:250:125–132 (1988).

Imamura et al., "Induction of in vitro tumor cell invasion of cellular monolayers by lysophosphatidic acid or phospholipase D", *Biochem. and Biophys. Res. Commun.* 193(2):497–503 (Jun. 15, 1993).

Martikainen et al., "Toxic effects of human pancreatic and snake and bee venom phospholipases A$_2$ on MCF–7 cells in culture", *Toxicon* 31(7):835–843 (1993).

Salari et al., "Stimulation of lipoxygenase product synthesis in human leukocytes and platelets by melittin", *Mol. Pharm.* 28:546–548 (1985).

Primary Examiner—Jeffrey E. Russel
Attorney, Agent, or Firm—Sterne, Kessler, Goldstein & Fox

[57] ABSTRACT

Methods of treating mammalian neoplastic disease are disclosed using phospholipase A$_2$ activating proteins and fragments thereof.

18 Claims, 5 Drawing Sheets

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
        ( A ) LENGTH: 325 amino acids
        ( B ) TYPE: amino acid
        ( C ) STRANDEDNESS: single
        ( D ) TOPOLOGY: linear     ( i i ) MOLECULE TYPE: peptide     ( x i ) SEQUENCE DESCRIPTION: SEQ ID NO:1:

```
Met  His  Tyr  Met  Ser  Gly  His  Ser  Asn  Phe  Val  Ser  Tyr  Val  Cys  Ile
 1              5                        10                       15
```

```
Ile Pro Ser Ser Asp Ile Tyr Pro His Gly Leu Ile Ala Thr Gly Gly
            20                  25                  30
Asn Asp His Asn Ile Cys Ile Phe Ser Leu Asp Ser Pro Met Pro Leu
        35                  40                  45
Tyr Ile Leu Lys Gly His Lys Asp Thr Val Cys Ser Leu Ser Ser Gly
    50                  55                  60
Lys Phe Gly Thr Leu Leu Ser Gly Ser Trp Asp Thr Thr Ala Lys Val
65                      70                  75                  80
Trp Leu Asn Asp Lys Cys Met Met Thr Leu Gln Gly His Thr Ala Ala
                85                  90                  95
Val Trp Ala Val Lys Ile Leu Pro Glu Gln Gly Leu Met Leu Thr Gly
            100                 105                 110
Ser Ala Asp Lys Thr Ile Lys Leu Trp Lys Ala Gly Arg Cys Glu Arg
        115                 120                 125
Thr Phe Leu Gly His Glu Asp Cys Val Arg Gly Leu Ala Ile Leu Ser
    130                 135                 140
Glu Thr Glu Phe Leu Ser Cys Ala Asn Asp Ala Ser Ile Arg Arg Trp
145                 150                 155                 160
Gln Ile Thr Gly Glu Cys Leu Glu Val Tyr Phe Gly His Thr Asn Tyr
            165                 170                 175
Ile Tyr Ser Ile Ser Val Phe Pro Asn Ser Lys Asp Phe Val Thr Thr
        180                 185                 190
Ala Glu Asp Arg Ser Leu Arg Ile Trp Lys His Gly Glu Cys Ala Gln
    195                 200                 205
Thr Ile Arg Leu Pro Ala Gln Ser Ile Trp Cys Cys Cys Val Leu Glu
210                 215                 220
Asn Gly Asp Ile Val Val Gly Ala Ser Asp Gly Ile Ile Arg Val Phe
225                 230                 235                 240
Thr Glu Ser Glu Glu Arg Thr Ala Ser Ala Glu Glu Ile Leu Ala Ser
            245                 250                 255
Leu Ser Arg Glu Ser Pro Leu Ile Ala Lys Val Leu Thr Thr Glu Pro
        260                 265                 270
Pro Ile Ile Thr Pro Val Arg Arg Thr Leu Pro Cys Arg Val Thr Arg
    275                 280                 285
Ser Met Ile Ser Ser Cys Leu Ser Arg Leu Val Ser Thr Ser Leu Ser
    290                 295                 300
Thr Ser Asp Ser His Leu Thr Ile Thr Ala Leu His Leu Phe Leu Thr
305                 310                 315                 320
Thr Thr Thr Thr Glu
            325
```

(2) INFORMATION FOR SEQ ID NO:2:

(i) SEQUENCE CHARACTERISTICS:
    (A) LENGTH: 14 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:2:

```
Lys Val Leu Thr Thr Glu Pro Pro Ile Ile Thr Pro Val Arg
1               5                   10
```

(2) INFORMATION FOR SEQ ID NO:3:

( i ) SEQUENCE CHARACTERISTICS:
    ( A ) LENGTH: 10 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:3:

Lys Val Leu Thr Thr Glu Pro Pro Ile Ile
1               5                   10

( 2 ) INFORMATION FOR SEQ ID NO:4:

( i ) SEQUENCE CHARACTERISTICS:
    ( A ) LENGTH: 11 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:4:

Thr Thr Glu Pro Pro Ile Ile Thr Pro Val Arg
1               5                   10

( 2 ) INFORMATION FOR SEQ ID NO:5:

( i ) SEQUENCE CHARACTERISTICS:
    ( A ) LENGTH: 8 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:5:

Lys Val Leu Thr Thr Glu Pro Pro
1               5

( 2 ) INFORMATION FOR SEQ ID NO:6:

( i ) SEQUENCE CHARACTERISTICS:
    ( A ) LENGTH: 6 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:6:

Lys Val Leu Thr Thr Gly
1               5

( 2 ) INFORMATION FOR SEQ ID NO:7:

( i ) SEQUENCE CHARACTERISTICS:
    ( A ) LENGTH: 12 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:7:

Val Leu Thr Thr Glu Pro Pro Ile Ile Thr Pro Val
1               5                   10

( 2 ) INFORMATION FOR SEQ ID NO:8:

( i ) SEQUENCE CHARACTERISTICS:
    ( A ) LENGTH: 13 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:8:

```
Val Leu Thr Thr Glu Pro Pro Ile Ile Thr Pro Val Arg
1               5                   10
```

( 2 ) INFORMATION FOR SEQ ID NO:9:

( i ) SEQUENCE CHARACTERISTICS:
        ( A ) LENGTH: 26 amino acids
        ( B ) TYPE: amino acid
        ( C ) STRANDEDNESS: single
        ( D ) TOPOLOGY: linear     ( i i ) MOLECULE TYPE: peptide     ( x i ) SEQUENCE DESCRIPTION: SEQ ID NO:9:

```
Cys Leu Glu Val Tyr Phe Gly His Thr Asn Tyr Ile Tyr Ser Ile Ser
1               5                   10                  15

Val Phe Pro Asn Ser Lys Asp Phe Val Thr
                20                  25
```

( 2 ) INFORMATION FOR SEQ ID NO:10:

( i ) SEQUENCE CHARACTERISTICS:
        ( A ) LENGTH: 26 amino acids
        ( B ) TYPE: amino acid
        ( C ) STRANDEDNESS: single
        ( D ) TOPOLOGY: linear     ( i i ) MOLECULE TYPE: peptide     ( x i ) SEQUENCE DESCRIPTION: SEQ ID NO:10:

```
Leu Glu Val Tyr Phe Gly His Thr Asn Tyr Ile Tyr Ser Ile Ser Val
1               5                   10                  15

Phe Pro Asn Ser Tyr Asp Phe Val Thr Thr
                20                  25
```

( 2 ) INFORMATION FOR SEQ ID NO:11:

( i ) SEQUENCE CHARACTERISTICS:
        ( A ) LENGTH: 26 amino acids
        ( B ) TYPE: amino acid
        ( C ) STRANDEDNESS: single
        ( D ) TOPOLOGY: linear     ( i i ) MOLECULE TYPE: peptide     ( x i ) SEQUENCE DESCRIPTION: SEQ ID NO:11:

```
Glu Gln Gly Leu Met Leu Thr Gly Ser Ala Asp Lys Thr Ile Lys Leu
1               5                   10                  15

Trp Lys Ala Gly Arg Cys Glu Arg Thr Phe
                20                  25
```

( 2 ) INFORMATION FOR SEQ ID NO:12:

( i ) SEQUENCE CHARACTERISTICS:
        ( A ) LENGTH: 26 amino acids
        ( B ) TYPE: amino acid
        ( C ) STRANDEDNESS: single
        ( D ) TOPOLOGY: linear     ( i i ) MOLECULE TYPE: peptide (x i) SEQUENCE DESCRIPTION: SEQ ID NO:12:

Phe Leu Gly His Glu Asp Cys Val Arg Gly Leu Ala Ile Leu Ser Glu
1               5                   10                  15

Thr Glu Phe Leu Ser Cys Ala Asn Asp Ala
            20              25

(2) INFORMATION FOR SEQ ID NO:13:

(i) SEQUENCE CHARACTERISTICS:
(A) LENGTH: 23 amino acids
(B) TYPE: amino acid
(C) STRANDEDNESS: single
(D) TOPOLOGY: linear (ii) MOLECULE TYPE: peptide (x i) SEQUENCE DESCRIPTION: SEQ ID NO:13:

Glu Ser Pro Leu Ile Ala Lys Val Leu Thr Thr Glu Pro Pro Ile Ile
1               5                   10                  15

Thr Pro Val Arg Arg Thr Leu
            20

REDUCTION OF MAMMALIAN NEOPLASMS WITH PHOSPHOLIPASE A2 ACTIVATING SUBSTANCES

BACKGROUND OF THE INVENTION

Mammalian response to injury or inflammation is a complex series of events. Shortly after an event which elicits an inflammatory cascade, the release of eicosanoids is initiated. The release of eicosanoids is mediated by the activation of Phospholipase $A_2$ ($PLA_2$) which releases arachidonic acid from phospholipids. Arachidonic acid is subsequently converted into the biologically active compounds known as eicosanoids. Prostaglandins, prostacyclines, leukotrienes and thromboxanes are all examples of eicosanoids. This series of events is often described as the arachidonic acid cascade.

Recently, a correlation has been shown between increased levels of phospholipase $A_2$ activating protein (PLAP) in vivo and rheumatoid arthritis. Research concerning PLAP and other initiators of the arachidonic acid cascade has recently shown that PLAP stimulates neutrophil aggregation and chemokinesis (Bomalaski et al., *J. Immuno.* 11:3957–3962 (1989)).

FIELD OF THE INVENTION

The present invention is directed to the field of mammalian neoplastic conditions. In particular, methods for reducing the severity of a neoplastic disease are provided which use agents which activate phospholipase $A_2$.

SUMMARY OF THE INVENTION

The present invention is based on the observation that agents which increase phospholipase A2 activity stimulate the recruitment/activation of cells of the immune system, Based on this observation, the present invention provides methods for treating neoplastic diseases. Specifically, tumor necrosis, the killing of neoplastic cells and a reduction in the size of a neoplastic mass, can be induced in a mammal suffering from a neoplastic disease by administering an effective amount of an agent which stimulates phospholipase $A_2$ activity or promotes arachidonic acid release, an indication of $PLA_2$ activity. The stimulation of phospholipase $A_2$ activity results in the generation of eicosanoids leading to the recruitment/activation of cell which promote an inflammatory response. The inflammatory response triggers the mammal's immune system to destroy the neoplastic cells. The response initiated by the treatment of the present invention results in a reduction in the severity of the neoplastic disease, a reduction of the tumor burden in the mammal, and a significant reduction in the number of neoplastic cells and neoplasm mass.

Phospholipase $A_2$ activating protein (PLAPs), and fragments thereof, are the preferred substances used in carrying out the present methods.

For a better understanding of the present invention, references made to the following detailed description and its scope will be pointed out in the appended claims.

BRIEF DESCRIPTION OF THE DRAWINGS

C6 glioma cells ($10^7$) were injected into rats and allowed to grow for two weeks. The average thickness of the tumors was approximately 7±2 mm in thickness. The animals were then treated with 500 µg of either agarose complexed PLAP peptide SEQ ID NO. 1 or agarose complexed PLAP-like peptide in which the two adjacent prolines were deleted. After three days of treatment, the animals were given a second injection of the peptide and the tumors were measured on day 6 of the treatment regimen. As can be seen in this figure, the proline-minus PLAP-like peptide, which failed to stimulate phospholipase $A_2$ activity in vitro (unpublished results) also failed to induce tumor regression. In contrast, the PLAP peptide which stimulated phospholipase $A_2$ activity had a profound effect on the size of the tumor.

C6 glioma cells ($10^7$) were injected into rats and allowed to grow for two weeks as in FIG. 1. By day 14, the tumors were approximately 7 mm in thickness. The animals were then given the indicated concentrations of the agarose complexed PLAP peptide. The thickness of the tumor was monitored after three days of treatment and the values are shown as a percentage of reduction in the tumor cell mass.

Sprague-Dawley rats were injected with $10^6$ C-6 glioma cells. The tumors were allowed to grow for 14 days prior to injection of 500 µg of agarose complexed PLAP peptide. Tumor thickness was measured after 3 and 6 days of treatment.

Balb C mice were injected with $10^6$ MTVL murine mammary tumor cells. The mice were treated with 200 µg of agarose complexed PLAP peptide 1 and 4 days after injection of the tumor cells. The animals were checked daily for survival. The results obtained are the average for twenty animals in each group. Animals that received no treatment (o), animals that received PLAP (●) $p<0.001$.

C57 Bl/6 mice were injected with $10^6$ LL-2 murine lung tumor cells. The mice were treated with 200 µg of agarose complexed PLAP peptide 1 and 4 days after injection of the tumor cells. The animals were checked daily for survival. The result obtained are the average for twenty animals in each group. Animals that received no treatment (o), animals that received PLAP (●) $p<0.0001$.

DETAILED DESCRIPTION OF THE INVENTION

The present invention is based on the unexpected observation that the induction of phospholipase $A_2$ ($PLA_2$) activity in a mammal suffering from a neoplastic disease, leads to a reduction in the severity of the neoplastic condition by stimulating the mammal's immune system cells to kill the neoplastic cells. Based on this observation, the present invention provides novel treatments for mammalian neoplastic diseases.

The present invention provides methods of stimulating cells of the immune system to kill neoplastic cells (tumor necrosis). The tumor necrosis brought about by the present methods leads to a decrease in the size of neoplastic mass and tumor burden within a mammal and increase in the survival time of the mammal.

In detail, the severity of a neoplastic disease can be reduced in a mammal suffering from a neoplastic disease by administering to the mammal a sufficient concentration of a phospholipase $A_2$ activating agent (PLAA) so as to induce PLA$_2$ activity. Induction of PLA$_2$ leads to the recruitment/ activation of the immune cells of the mammal.

amino acid sequence of PLAP is:

Met His Tyr Met Ser Gly His Ser Asn Phe Val Ser Tyr Val Cys Ile Ile Pro Ser Ser Asp Ile

Tyr Pro His Gly Leu Ile Ala Thr Gly Gly Asn Asp His Asn Ile Cys Ile Phe Ser Leu Asp Ser

Pro Met Pro Leu Tyr Ile Leu Lys Gly His Lys Asp Thr Val Cys Ser Leu Ser Ser Gly Lys Phe

Gly Thr Leu Leu Ser Gly Ser Trp Asp Thr Thr Ala Lys Val Trp Leu Asn Asp Lys Cys Met

Met Thr Leu Gln Gly His Thr Ala Ala Val Trp Ala Val Lys Ile Leu Pro Glu Gln Gly Leu Met

Leu Thr Gly Ser Ala Asp Lys Thr Ile Lys Leu Trp Lys Ala Gly Arg Cys Glu Arg Thr Phe

Leu Gly His Glu Asp Cys Val Arg Gly Leu Ala Ile Leu Ser Glu Thr Glu Phe Leu Ser Cys Ala

Asn Asp Ala Ser Ile Arg Arg Trp Gln Ile Thr Gly Glu Cys Leu Glu Val Tyr Phe Gly His Thr

Asn Tyr Ile Tyr Ser Ile Ser Val Phe Pro Asn Ser Lys Asp Phe Val Thr Thr Ala Glu Asp Arg

Ser Leu Arg Ile Trp Lys His Gly Glu Cys Ala Gln Thr Ile Arg Leu Pro Ala Gln Ser Ile Trp

Cys Cys Cys Val Leu Glu Asn Gly Asp Ile Val Val Gly Ala Ser Asp Gly Ile Ile Arg Val Phe

Thr Glu Ser Glu Glu Arg Thr Ala Ser Ala Glu Glu Ile Leu Ala Ser Leu Ser Arg <u>Glu Ser Pro</u>

<u>Leu Ile Ala Lys Val Leu Thr Thr Glu Pro Pro Ile Ile Thr Pro Val Arg Arg</u> Thr Leu Pro Cys

Arg Val Thr Arg Ser Met Ile Ser Ser Cys Leu Ser Arg Leu Val Ser Thr Ser Leu Ser Thr Ser

Asp Ser His Leu Thr Ile Thr Ala Leu His Leu Phe Leu Thr Thr Thr Thr Thr Glu; (SEQ ID NO: 1).

As used herein phospholipase A$_2$ activating agents, PLAA, are defined as agents which induce phospholipase A$_2$ activity. A variety of procedures are known in the art for assaying an agent for PLAA activity. These include, but are not limited to, assaying cultured endothelial cells or smooth muscle cells for the release of arachidonic acid in the presence of the agent as well as cell free systems which utilize 1-palmitoyl-2-[14C]arachidonyl-sn-glycero-3-phospho-[methy13H]choline to assay for PLA$_2$ activity (see Clark et al., *J. Biol. Chem.* 261:10713–10718 (1986) and Clark et al., *Biochem. J.* 250:125–132 (1988).

The preferred class of PLAA of the present invention are proteins which act as PLAAs. Several proteins known in the art have PLAA activity. One class of these proteins is known as phospholipase A2 activating protein (PLAP). The isolation, identification and synthesis of one member of this family, mouse PLAP (PLAP), is described in U.S. Pat. No. 5,294,698, the contents of which are incorporated by reference herein.

Other proteins which are known PLAPs are TNF-alpha, and melittin. These proteins have been shown to stimulate PLA$_2$ activity (Salari et al., *Mol. Pharm.* 28:546 (1985)).

The most preferred PLAAs for use in the present method are based on, or derived from, mouse phospholipase A$_2$ polypeptide, PLAP (Clark et al., *PNAS USA* 88:5418–5422 (1991)). PLAP has a molecular mass of approximately 28,000 as determined by SDS gel electrophoresis. The Fragments of PLAP having PLA$_2$ stimulating activity can also be used in the present methods. As used herein, a fragment of PLAP is defined as a polypeptide having fewer amino acids than PLAP but retaining the native molecule's ability to stimulate PLA$_2$, although this may be at a decreased efficiency. The preferred fragments of PLAP are from about six to about 30 amino acids in length, the most preferable having about 22 amino acids in length. Clark et al., *PNAS USA* 88:5418–5422 (1991) describes the generation of fragments of PLAP which maintain PLA$_2$ activity.

The amino acid sequence of PLAP shows significant sequence homology with melittin in the regions around amino acids 131 and 132, amino acids 191–193, and amino acids 260 through 280. Melittin is a low molecular weight peptide containing 26 amino acids found in bee venom that has phospholipase activating activity. Fragments of PLAP selected to contain at least a portion of the amino acids in one of the conserved regions are preferred, more preferably the fragment contains at least half to all of the amino acids in one of these regions.

Fragments may be selected by using one of the aforementioned homologous regions as a starting point and proceeding either towards the amino terminus or the carboxyl terminus of PLAP for the desired number of amino acids, and constructing a fragment or peptide having the corresponding amino acid sequence. It is well recognized that amino acid sequences may be modified in various ways yet still retain the desired fundamental activity. Those portions of a desired sequence which are not essential for PLA$_2$-activation can be deleted, altered or otherwise modified.

Fragments of PLAP may be prepared by any method known in the art or preparing peptides. These include, but are not limited to, chemical synthesis, recombinant DNA techniques, and cleavage of isolated PLAP. Chemical synthesis of the fragments or peptides is presently preferred for convenience of preparation. Solid phase synthesis apparatus such as the Milligen/Biosearch 9600 peptide synthesizer, for example, have been used to synthesize fragments of rPLAP.

A non-limiting list of PLAP fragments which can be used in the present invention includes, but is not limited to:
Lys -Val-Leu-Thr-Thr-Glu-Pro-Pro-Ile-Ile-Thr-Pro-Val-Arg (SEQ ID NO: 2);
Lys-Val-Leu-Thr-Thr-Glu-Pro-Pro-Ile-Ile (SEQ ID NO: 3);
Thr-Thr-Glu-Pro-Pro-Ile-Ile-Thr-Pro-Val-Arg (SEQ ID NO: 4);
Lys-Val-Leu-Thr-Thr-Glu-Pro-Pro (SEQ ID NO: 5);
Lys-Val-Leu-Thr-Thr-Glu (SEQ ID NO: 6);
Val-Leu-Thr-Thr-Glu-Pro-Pro-Ile-Ile-Thr-Pro-Val (SEQ ID NO: 7);
Val-Leu-Thr-Thr-Glu-Pro-Pro-Ile-Ile-Thr-Pro-Val-Arg (SEQ ID NO: 8);
Cys-Leu-Glu-Val-Tyr-Phe-Gly-His-Thr-Asn-Tyr-Ile-Tyr -Ser-Ile-Ser-Val-Phe-Pro-Asn-Ser-Lys-Asp-Phe-Val-Thr (SEQ ID NO: 9);
Leu-Glu-Val-Tyr-Phe-Gly-His-Thr-Asn-Tyr-Ile-Tyr-Ser -Ile-Ser-Val-Phe-Pro-Asn-Ser-Lys-Asp-Phe-Val-Thr-Thr (SEQ ID NO: 10);
Glu-Gln-Gly-Leu-Met-Leu-Thr-Gly-Ser-Ala-Asp-Lys-Thr -Ile-Lys-Leu-Trp-Lys-Ala-Gly-Arg-Cys-Glu-Arg-Thr-Phe (SEQ ID NO: 11); and
Phe-Leu-Gly-His-Glu-Asp-Cys-Val-Arg-Gly-Leu-Ala-Ile -Leu-Ser-Glu-Thr-Glu-Phe-Leu-Ser-Cys-Ala-Asn-Asp-Ala (SEQ ID NO: 12).

As described above, PLAPs can be isolated based on biological activity using known assay methods. Alternatively, PLAPs can be isolated by screening DNA or expression libraries with probes which recognize DNA or amino acid sequences found to be homologous amongst known PLAP family members. See Sambrook et al., *Molecular Cloning, A Laboratory Manual,* second edition, Cold Spring Harbor Laboratory Press, Cold Spring Harbor, New York, 1989.

The murine smooth muscle-like brain tumor cell line BC3H1, obtained from the American Type Culture Collection (accession number CRL 1443), was used in the isolation of the sequence encoding rPLAP. Other types of mammalian cells and cell lines, such as human cells and bovine cell lines, may be used for isolation of a nucleic acid sequence encoding a PLAP. Using the DNA sequences encoding PLAP, a skilled artisan can readily isolate the human homologue of PLAP from human cells. PLAP isolated from any source is suitable for use in the present methods described herein so long as the PLAP stimulates PLA$_2$ activity in the mammal undergoing treatment.

Another preferred class of PLAAs comprises low molecular weight organic compounds designed to mimic the structure of a proteinaceous PLAA. Methods for designing these compounds, sometimes referred to as peptidomimetics, are described in Peters et al., *Biotechnology* 12:147–150 (1994).

The PLAAs used in the the present invention, include, but are not limited to, peptides, carbohydrates, vitamin derivatives, or other pharmaceutical agents. These agents can be selected and screened at random or rationally selected or designed using protein modeling techniques.

For random screening, agents such as peptidomimetic peptides, carbohydrates, pharmaceutical agents and the like are selected at random and are assayed for their ability to stimulate phospholipase as described above and below. Alternatively, agents may be rationally selected or designed. As used herein, an agent is said to be "rationally selected or designed" when the agent is chosen based on the configuration of known PLAP/receptor interactions. For example, one skilled in the art can readily adapt currently available procedures to generate antibodies, peptides, pharmaceutical agents and the like capable of binding to a specific peptide sequence such as the active regions of the PLAPs herein described, for example see Hurby et al., Application of Synthetic Peptides: Antisense Peptides", In *Synthetic Peptides, A User's Guide,* W. H. Freeman, N.Y., pp. 289–307 (1992), and Kaspczak et al., *Biochemistry* 28:9230-8 (1989) and Harlow, *Antibodies,* Cold Spring Harbor Press, N.Y. (1990).

Once a PLAA is chosen for use in the present methods, a variety of techniques are available to produce the agent. Peptide agents which occur naturally can be purified from cells or fluids which contain the agent. For example, PLAP can be purified from fluids using the methods disclosed in U.S. Pat. No. 5,294,698. One fluid which has been shown to possess high levels of PLAP is synovial fluid from a patient suffering from rheumatoid arthritis.

The PLAPs used in the present methods can alternatively be purified from cells which have been altered to express the PLAP. As used herein, a cell is defined as having been altered to produce PLAP if the cells have been subjected to recombinant DNA techniques so as to produce a higher level of PLAP than that found in non-altered cells. A variety of host/vector systems are known in the art and can readily be adapted to produce the agents used in the present methods. For example, see Sambrook et al., *A Laboratory Manual,* Cold Spring Harbor Laboratory Press (1989)) for a detailed description on the use of procaryotic cells to express a desired protein.

In addition to prokaryotic hosts, eukaryotic hosts such as yeast cells, mammalian cells and insect cells have been successfully used to produce proteins of a known sequence. For example see *The Molecular Biology of the Yeast Saccharomyces,* part I, 181–209 (1981), Cold Spring Harbor Laboratory). Because post-translational modifications, such as disulfide bridge formation, glycosylation, phosphorylation and/or oligomerization, are frequently necessary for the expression of biologically active eukaryotic proteins, it may be desirable to produce the larger peptide agents used in the present methods in mammalian host systems.

The agents used in the present methods have the demonstrated ability to initiate a vigorous inflammatory response by stimulating PLA$_2$ activity. The inflammatory response which is induced reduces tumor burden and increases survival time in a mammal possessing neoplastic growth by promoting leukocyte infiltration into tissues, including macrophages and natural killer cells, and inducing the release of significant amounts of prostaglandins, such as PGE$_2$.

Because the agents used in the present invention initiate an inflammatory cascade regardless of the type of neoplastic growth which is present in the mammal, the present methods are suitable for use in treating a wide variety of neoplasm types. These include, but are not limited to, tumors of the organs, soft tissue sarcomas, neuroblastomas, gliomas, myelomas and lymphomas. A skilled artisan can readily apply the present methods in the therapeutic treatment of a variety of neoplastic disease. The examples which follow demonstrate the effectiveness of the present methods in stimulating tumor necrosis of glioma cells, neoplastic mammary cells, and neoplastic lung cells.

The agents used in the present methods are intended to be provided to a mammal in an amount sufficient to stimulate $PLA_2$ activity. The induction of $PLA_2$ leads to the production of arachidonic acid, inducing the recruitment/activation of cells of the immune system. As such, the agents used in the present invention reduce the severity of a neoplastic disease by stimulating neoplastic cell killing.

The agent is administered in an amount which is said to be therapeutically effective (and hence sufficient to stimulate neoplastic cell killing) when the dosage, route of administration, etc. of the agent is sufficient to stimulate recruitment and activation of cells of the immune system leading to a reduction in neoplastic cell number and/or neoplastic cell mass. Such an effect can be assayed indirectly by examining $PLA_2$ activity, for example by assaying for arachidonic acid release, or directly by determining neoplastic cell number or neoplasm size in the mammal undergoing treatment before and following administration. Alternatively, the effectiveness of any particular agent can first be assessed using known animal models, such as those utilized in the examples which follow.

The administration of agents in the present methods may be for either "prophylactic" or "therapeutic" purposes. When provided therapeutically, the agent is provided at (or shortly after) the onset or detection of neoplastic growth within the mammal. The therapeutic administration of the agents serves to reduce the number of neoplastic cells present and to reduce the mass of the neoplasm within the mammal.

When provided prophylactically, the agent is provided in advance of the appearance of neoplastic cells. The prophylactic administration of the agent serves to prevent the appearance of neoplastic cells. The prophylactic use of the present methods is especially suitable when there is a genetic preponderance for neoplastic growth within the mammal's family history.

The agents used in the present methods are intended to be provided to a mammal as a means of reducing tumor burden and decreasing the mass (size) of the neoplastic growth, by providing a means of using the immune system of the mammal to kill tumor cells. In providing a mammal with one or more PLAAs, the dosage of the agent which is to be administered will vary depending upon such things as the nature of the agent, the route of administration, the patient's age, weight, height, sex, general medical condition, previous medical history. Although numerous factors need to be considered, a skilled artisan can readily adapt a given agent for the intended use using known formulation procedures.

Techniques of dosage determination and administration are well known in the art for peptide agents. In general, it is desirable to provide a mammalian patient with a dosage of a peptide agent in the range of from about 1 pg/kg to 10 mg/kg (body weight of patient). The therapeutically effective dose can be lowered if the PLAA is administered with other anti-tumor agent or another immuno-stimulatory agent. As used herein, one agent is said to be administered with another agent when the administration of the two agents is in such proximity of time that both agents, or the effect they elicit, can be detected at the same time within the mammal.

The agents used in the present methods, when administered as a therapeutic agent, may be administered to the mammal by any means so long as $PLA_2$ activity is induced within the mammal. Such methods include, but are not limited to, intravenous, intramuscular, subcutaneous, enteral, or parenteral delivery systems. When administering the agent via injection, the administration may be by continuous infusion, or by single or multiple boluses. When administering an agent orally, the agent may contain in addition to carriers, additives such as sodium citrate, calcium carbonate and dicalcium phosphate together with various additives such as starch, preferably potato starch, gelatine and the like. Furthermore, lubricants such as magnesium stearate, sodium laurylsulphate and talc can be used to form tablets. In the case of aqueous suspensions, the active substances may contain, in addition to the above-mentioned excipients, various flavor improvers or colorings.

Dramatic responses have been observed when PLAAs are administered directly into a cancerous lesion. In these situations, prompt reduction in tumor load is observed as a result of massive macrophage and natural killer cell infiltration. As such, a preferred method of administering the agents used in the present methods is to supply the agent to the site of the neoplastic growth, for example by directly injecting the agent into the neoplastic growth or providing the agent in a controlled release formulation to tissues in close proximity to the neoplastic growth. A skilled artisan can readily formulate the agents of the present invention so as to ensure that an effective amount of the agent is provided and maintained at the site of neoplastic growth.

The agents of the present invention can be formulated according to known methods to prepare pharmaceutically acceptable compositions. There exist a wide variety of procedures, whereby the agents used in the present methods, are combined in admixture with a pharmaceutically acceptable carrier vehicle. Suitable vehicles and their formulation, inclusive of other human proteins, e.g., human serum albumin, are well known in the art. In order to form a pharmaceutically acceptable composition suitable for effective administration, such compositions will contain an effective amount of one or more of the PLAA agents of the present invention.

The agents used in the present methods can also be administered as part of a polyethylene glycol-peptide conjugate (e.g. PEG-PLAP). For example, PLAP can be conjugated with one or more strands of activated PEG to provide long-acting therapeutics. One preferred form of activated PEG is polyethylene glycol-succinimidyl carbonate, disclosed in commonly-assigned U.S. Pat. No. 5,122,614, the contents of which are incorporated by reference herein. Liposomes containing the PLAP peptides can also be administered in accordance with the invention.

Additional known pharmaceutical methods may be employed to control the duration of action of the PLAAs used in the present methods. Control release preparations may be achieved through the use of polymers to complex or absorb the agents used in the present methods. A controlled delivery system can be used by incorporating the agent in an appropriate macromolecule (for example polyesters, polyamino acids, polyvinyl, pyrrolidone, ethylenevinylacetate, methylcellulose, carboxymethylcellulose, or protamine sulfate).

Another method to control the duration of action by controlled release preparations is to incorporate the agent into particles of a polymeric material such as agarose beads, polyesters, polyamino acids, hydrogels, poly(lactic acid) or ethylene vinyl acetate copolymers. Alternatively, instead of incorporating these agents into polymeric particles, it is possible to entrap these materials in microcapsules prepared, for example, by coacervation techniques or by interfacial polymerization, for example, hydroxymethylcellulose or gelatine-microcapsules and poly(methylmethacylate) microcapsules, respectively, or in colloidal drug delivery systems, for example, liposomes, albumin microspheres, microemulsions, nanoparticles, and nanocapsules or in macroemulsions.

The use of control release formulation allows a skilled artisan to directly implant the PLAA in close proximity to the site of the neoplasm. The placing of a PLAA within close proximity to the site of the neoplasm allows for the preferential recruitment/activation of cells to this site. Such formulation reduces the amount of agent needed to achieve therapeutic effectiveness.

Other methods which have been developed for targeting an agent to neoplastic cells can be applied to the agents used in the present methods. For example, the agents used in the present methods can be formulated into a composition which selectively targets the agent to the neoplastic cells. Antibodies, single chain antibodies, and antibody fragments, which preferentially bind to the neoplastic cells, have been conjugated with other anti-neoplastic agents as a means of selectively targeting the agent to the desired site of action. Using techniques such as these which are known in the art, a skilled artisan can readily fuse rPLAP, of a fragment thereof, to a monoclonal antibody or single chain antigen binding molecule to target delivery.

Having now described the invention, the following examples serve to provide further appreciation of the present invention. The examples are not meant in any way to restrict the effective scope of the invention.

EXAMPLE 1

Synthesis of Phospholipase $A_2$ Activating Protein (PLAP) Peptide

Synthetic PLAP peptide was synthesized by t-butoxycarbonyl chemistry, on a Milligen/Biosearch 9600 peptide synthesizer in accordance with the manufacturer's instructions to give a peptide of 21 amino acids having the sequence:

GLU-SER-PRO-LEU-ILE-ALA-LYS-VAL-LEU-THR-THR-GLU-PRO -PRO-ILE-ILE-THR-PRO-VAL-ARG-ARG-(THR-LEU) (SEQ ID NO: 13)

The released PLAP peptide was purified via reverse phase HPLC to give purified peptide. A WATERS™ C18 column using 0–60% acetonitrile gradient was used to purify the PLAP peptides.

Preparation of PLAP Peptide for Injection

The PLAP peptide prepared above was dissolved in sterile saline and bound overnight to Affi-gel Blue agarose beads, a product of BioRad, Melville, N.Y., until a final concentration of 125 micrograms of PLAP/ml of agarose beads was obtained. Prior to peptide binding, the beads were extensively washed in sterile deionized water to remove endotoxin contamination.

Preparation of Rat-Air Pouch G6 Glioma Model i. Culture of glioma cells

G6 glioma cells, derived from a glioma induced in the Wistar strain of rat and obtained from the American Type Culture Collection (ATCC) were maintained in tissue culture. The cell cultures were grown to confluence in 75 cm$^2$ tissue culture flasks, detached from the flasks by addition of trypsin/EDTA, washed twice in fresh culture medium, and resuspended at a final concentration of $2 \times 10^6$ cells per ml.

ii. Induction of the air pouch

Air pouches were formed in female Sprague-Dawley rats (average age 6–8 weeks; average weight 180 grams). Briefly, 20 cc's of sterile air was injected into the subcutaneous tissues on the dorsum of the animal to form an air filled pouch. Inflation of the pouches was maintained by re-injection of sterile air every other day. Pouches were ready for use on day 7.

iii. Formation of gliomas

Suspension of cultured glioma cells ($1 \times 10^6$–$1 \times 10^7$ cells) were injected into the air pouches. By day 14, the tumors typically were of sufficient size to be used as described below.

Administration of PLAP Peptide and Control

Animals were injected with 500 µgrams of PLAP peptide bound to agarose beads. A similar number of rats were injected with unmodified agarose beads as a control. In order to ensure uniform distribution of the bound peptide, the total volumes injected were increased to 5 ml by the addition of sterile saline immediately prior to injection. Since tumor growth was characterized by formation of large effusions containing high levels of eicosanoids, the tumors were aspirated immediately prior to injection of PLAP peptide or agarose beads alone.

Seventy-two hours after injection, the animals were euthanized by using $CO_2$ gas. The tumor effusions were aspirated and the tumor cell numbers were determined using a Coulter counter. The samples were frozen and stored at −80° for later eicosanoid assay. The tumor masses were removed through an incision made in the dorsum of the animal and weighed. Samples of tumor tissues were stored in formalin for routine histology or snap-frozen in liquid $N_2$ for immunocytochemistry.

Histologic Analysis of Tumors

Formalin-fixed tumor tissues were embedded, sectioned and reacted with hematoxylin and eosin according to standard methods. Sections were mounted and examined in an Olympus light microscope.

Immunocytochemical Analysis of Tumors

Snap-frozen tissue samples were sectioned on a cryotome, fixed in acetone, blocked with levamisole, and then reacted with monoclonal antibodies to cell surface determinants expressed by mononuclear cells. After washing, tissue sections were reacted with biotin-labelled rat anti-mouse IgG monoclonal antibodies, alkaline phosphate-labelled avidin-biotin complex (ABC, Vecta, Burlinghame, Calif.) and color developed by the addition of appropriate substrate. Sections were then mounted in Permount (Fisher Scientific) and read in an Olympus light microscope.

Measurement of Eicosanoids in Tumor Exudates

Eicosanoid levels in exudates obtained from tumors were determined using enzyme-lined immunoassay kits purchased from Cayman Chemical Company (Ann Arbor, Mich.) and used as recommended by the supplier. Calculations of the amounts of eicosanoids were made using EPA software purchased from the same company.

Results and Discussion

Figure 1:
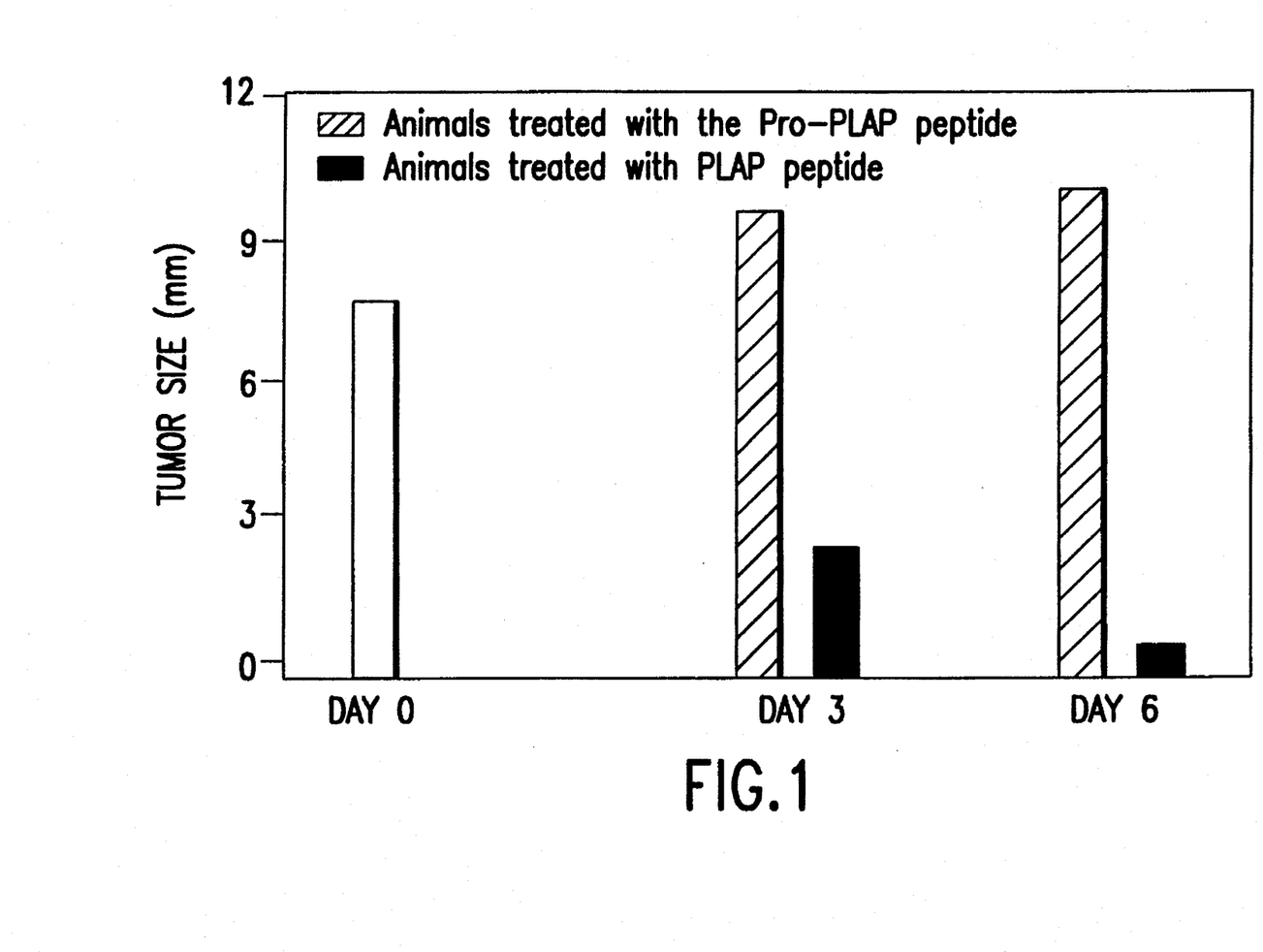
FIG. 1. The effects of a PLAP peptide on tumor regression.
Figure 2:
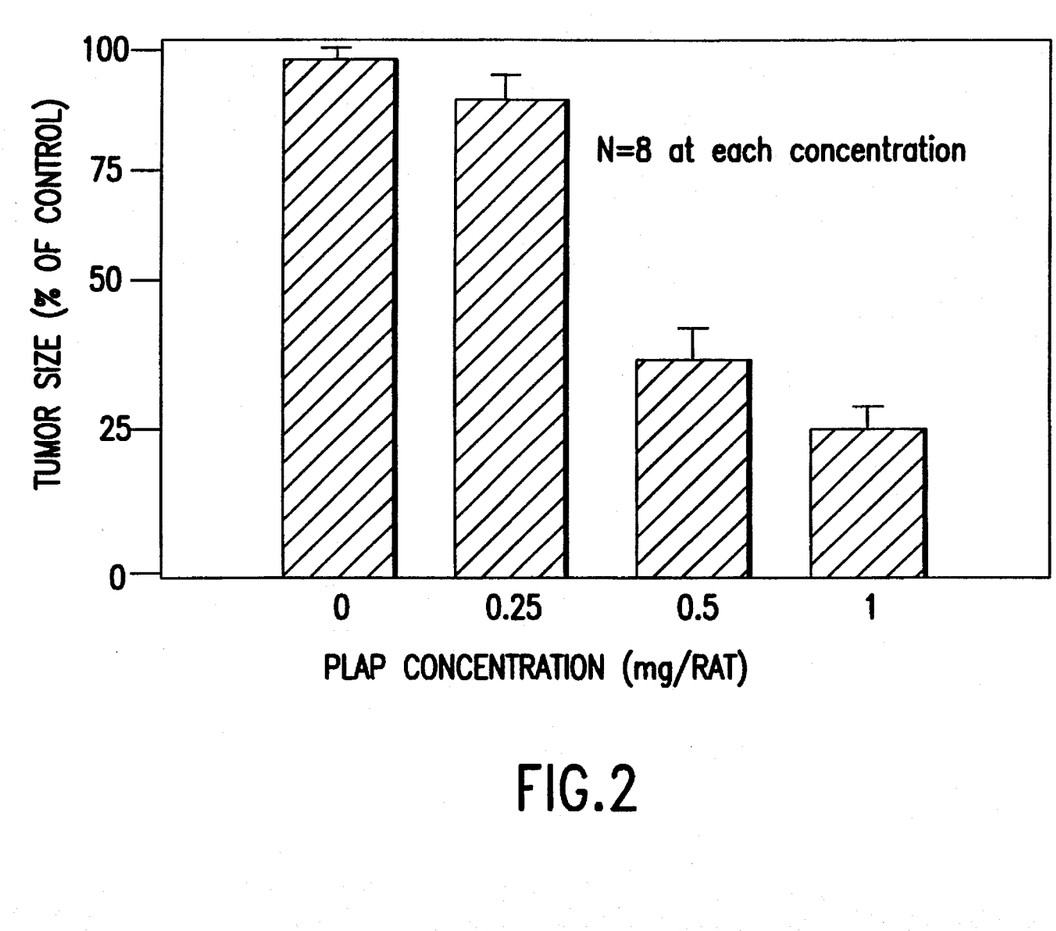
FIG. 2. Dose dependent response of tumor regression.

Injection of PLAP peptide coupled to agarose beads, which provides a sustained release of the peptide, caused significant necrosis in tumor tissues examined after 72 hours. There was a reduction in tumor weight compared with control animals (FIGS. 1 and 2). These effects were not observed when agarose beads alone were injected into tumors (results not presented). Moreover, injection of a synthetic modified PLAP-like peptide without $PLA_2$ enzyme activating activity, did not cause tumor necrosis (FIG. 1). Thus, PLAP peptide induces tumor necrosis in a manner which appears to be dependent on increased $PLA_2$ enzyme activity.

In addition, the amount of leukotriene $B_4$ ($LTB_4$) was 20-fold greater and $PGE_2$ was 50-fold greater in PLAP peptide treated tumors compared with tumors injected with agarose beads. No changes were observed in the amounts of $PGI_2$, and $LTC_4$ in exudates from tumors treated with PLAP peptide compared with those injected with agarose beads.

EXAMPLE 2

To determine whether PLAP-induced tumor necrosis was associated with specific cellular events, frozen sections of tumor tissues were reacted with MAbs directed at subpopulations of mononuclear cells. Injection of PLAP peptide stimulated mononuclear cell infiltrate, which comprised high numbers of OXI (cytotoxic T lymphocyte), and NRK-1 positive (NK) cells. Injection of agarose beads alone did not cause a similar mononuclear cell infiltrate. Thus, PLAP-induced tumor necrosis appears to be mediated through enhanced NK/LAK cell activation.

EXAMPLE 3

To determine the effect of concentration of PLAP peptide on tumor cell number and tumor size, Sprague-Dawley rats were injected with $10^6$ C-6 glioma cells as described above, and were then treated with either 0, 0.25, 0.5, or 1 mg/rat PLAP. Three days after treatment, the maximum thickness of the tumors was measured.

FIG. 2 provides the average result obtained using 8 animals in each treatment group. The reduction in tumor size was found to be concentration dependent, with the maximum effectiveness being obtained with the highest amount of PLAP peptide administered.

EXAMPLE 4

To determine the length of the effectiveness of administering PLAP peptide, Sprague-Dawley rats were injected with $10^6$ C-6 glioma cells as described above. The tumors were allowed to grow for 14 days prior to injection of 500 µg of agarose bound PLAP peptide. Tumor thickness was measured 3 and 6 days after treatment.

Figure 3:
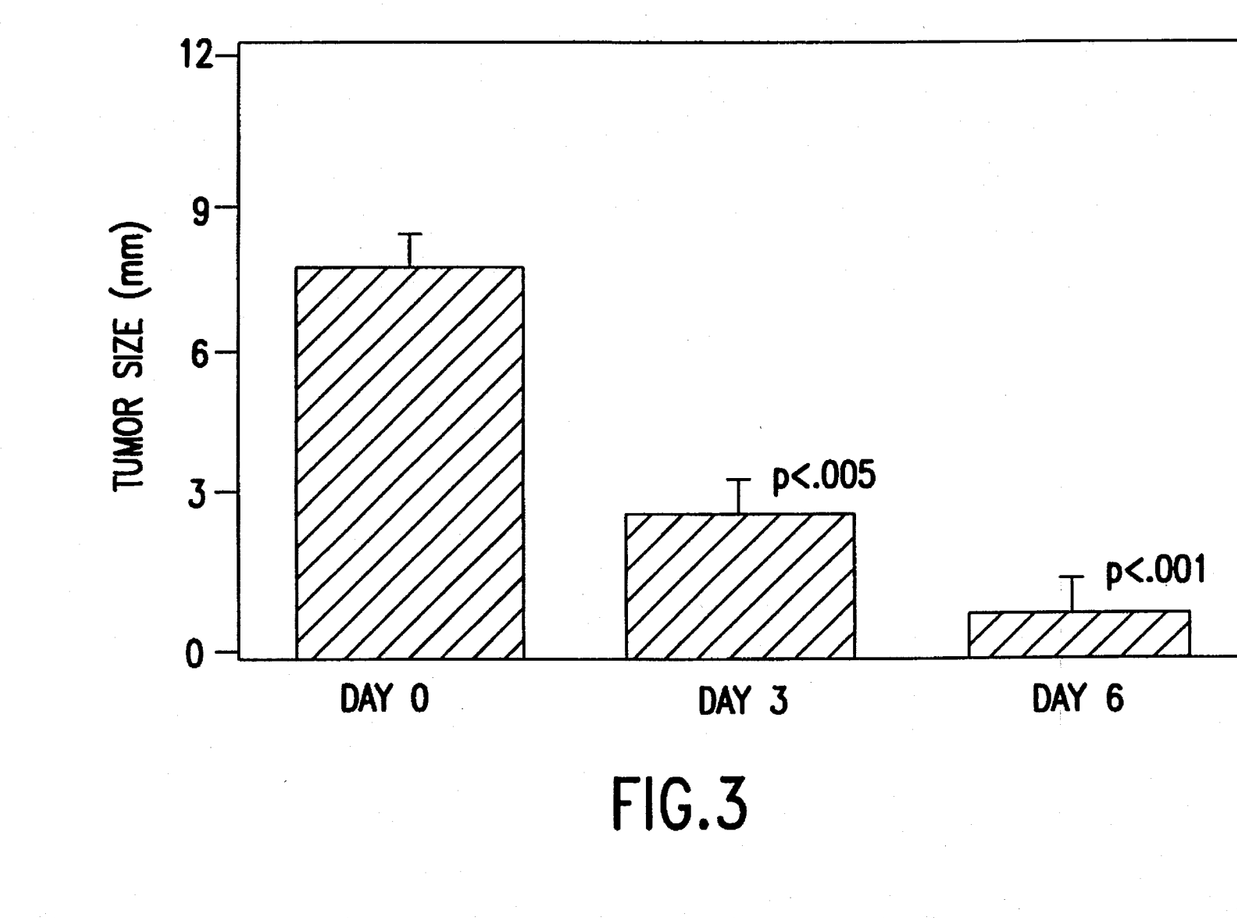
FIG. 3. Time course of the effectiveness of administering PLAP.

FIG. 3 provides the result obtained, the values shown representing the means and standard deviations of tumor thickness in 8 animals. Tumor necrosis was observed to continue even at 6 days following treatment.

EXAMPLE 5

Figure 4:
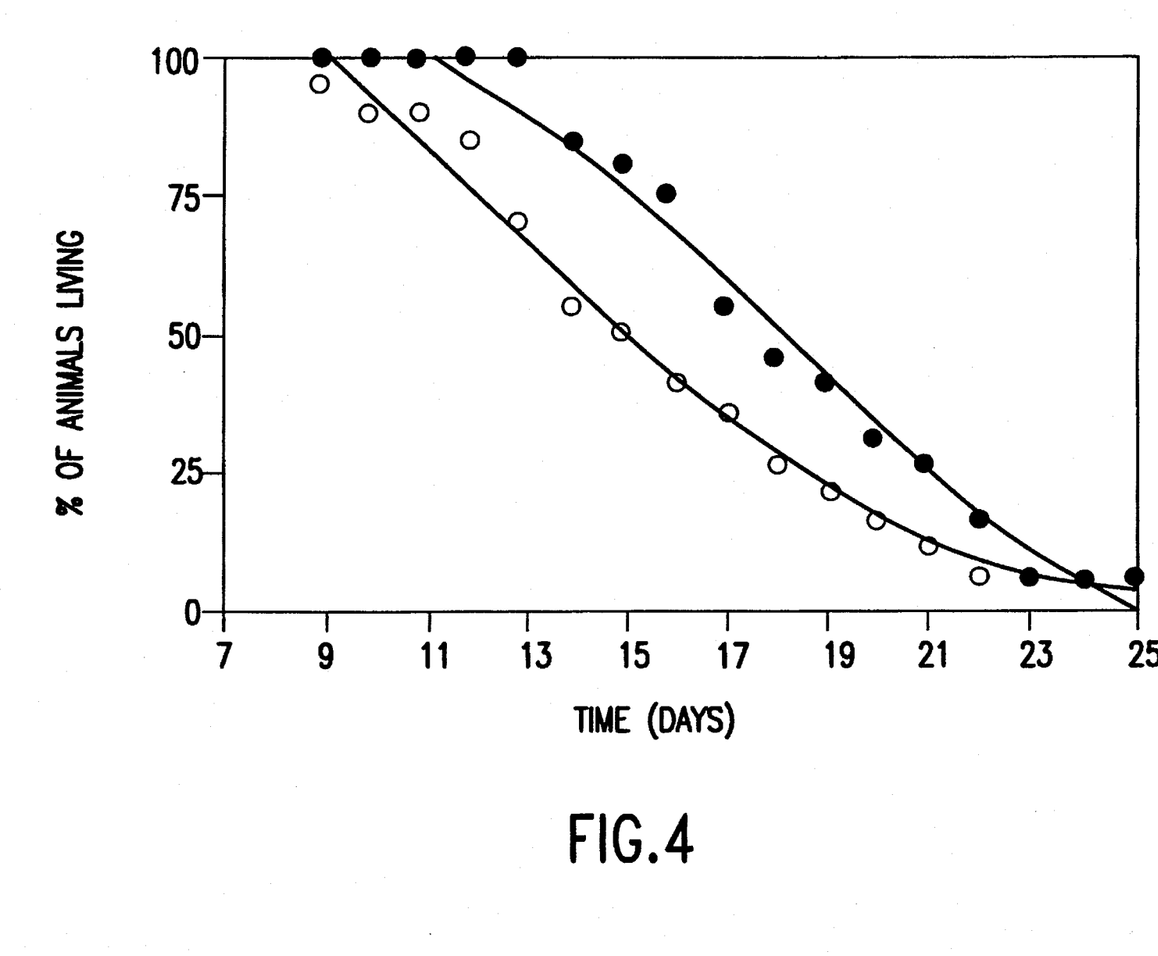
FIG. 4. The effectiveness of PLAP on mammary tumor cells.

The effectiveness of stimulating tumor necrosis for tumors other than gliomas was tested. To test effectiveness of the present methods in treating neoplastic mammary cells, Balb C mice were injected with $10^6$ MTVL murine mammary tumor cells as described above for the glioma cells. The mice were treated with 200 µg of agarose bound PLAP peptide 1 and 4 days after injection of the tumor cells. The animals were checked daily for survival. FIG. 4 provides the average of the results obtained for twenty animals in each group. PLAP peptide increased the survival of mice injected with mammary tumor cells compared to control animals treated with agarose beads alone, FIG. 4.

Figure 5:
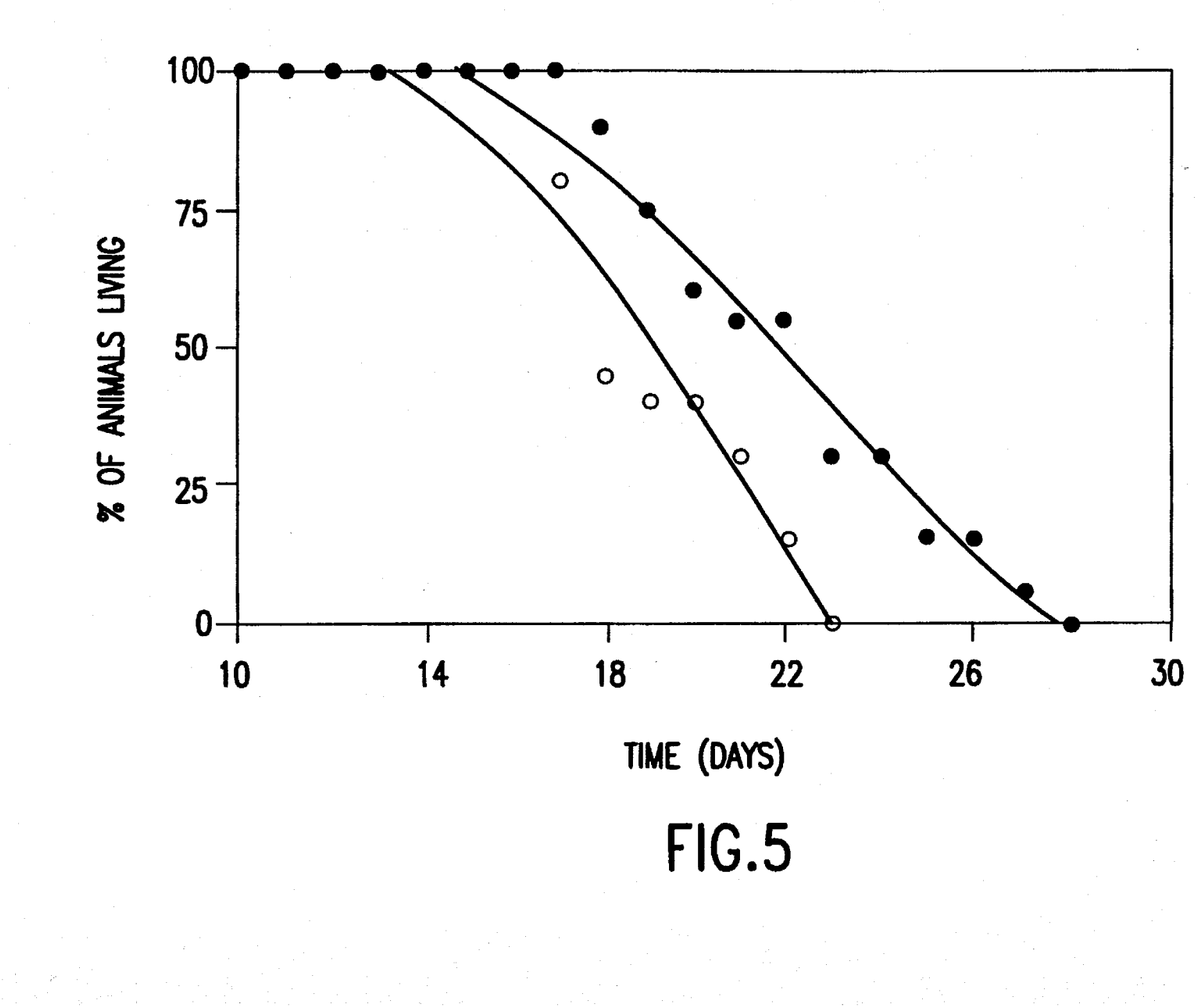
FIG. 5. The effectiveness of PLAP on lung tumor cells

To test the effectiveness of the present methods in treating neoplastic lung cells, C57 Bl/6 mice were injected with $10^6$ LL-2 murine lung tumor cells as described above for the glioma cells. The mice were treated with 200 µg of agarose bound PLAP peptide 1 and 4 days after injection of the tumor cells. The animals were checked daily for survival. FIG. 5 provides the average of the result obtained for twenty animals in each group were used.

PLAP peptide increased the survival of mice injected with lung tumor cells when compared to control animals treated with agarose beads alone.

All publications mentioned hereinabove are hereby incorporated in their entirety by reference.

While the foregoing invention has been described in some detail for purposes of clarity and understanding, it will be appreciated by one skilled in the art from a reading of this disclosure that various changes in form and detail can be made without departing from the true scope of the invention and appended claims.

---

What is claimed is:

1. A method of reducing the severity of neoplastic growth in a mammal suffering from a neoplastic disease comprising the step of administering to said mammal an effective amount of a phospholipase A₂ activating agent, wherein said phospholipase A₂ activating agent is selected from the group consisting of phospholipase A₂ activating polypeptide SEQ ID No: 1, and fragments thereof which retain phospholipase A₂ activating activity.

2. The method of claim 1, wherein said fragment of phospholipase A₂ activating polypeptide comprises the amino acid sequence:

GLU-SER-PRO-LEU-ILE-ALA-LYS-VAL-LEU-THR-THR-GLU-PRO -PRO-ILE-ILE-THR-PRO-VAL-ARG-ARG-; (residues 1–21 of SEQ ID NO: 13).

3. The method of claim 1, wherein said fragment of phospholipase A₂ activating polypeptide comprises an amino acid sequence selected from the group consisting of:

Lys-Val-Leu-Thr-Thr-Glu-Pro-Pro-Ile-Ile-Thr-Pro-Val -Arg (SEQ ID NO: 2);

Lys-Val-Leu-Thr-Thr-Glu-Pro-Pro-Ile-Ile (SEQ ID NO: 3);

Thr-Thr-Glu-Pro-Pro- Ile- Ile-Thr-Pro-Val -Arg (SEQ ID NO: 4);

Lys-Val-Leu-Thr-Thr-Glu-Pro-Pro (SEQ ID NO: 5);

Lys-Val-Leu-Thr-Thr-Glu (SEQ ID NO: 6);

Val -Leu-Thr-Thr-Glu- Pro-Pro- Ile- Ile-Thr-Pro-Val (SEQ ID NO: 7);

Val-Leu-Thr-Thr-Glu-Pro-Pro-Ile-Ile-Thr-Pro-Val-Arg (SEQ ID NO: 8);

Cys-Leu-Glu-Val-Tyr-Phe-Gly-His-Thr-Asn-Tyr-Ile-Tyr -Ser-Ile-Ser-Val-Phe-Pro-Asn-Ser-Lys-Asp-Phe-Val-Thr (SEQ ID NO: 9);

Leu-Glu-Val-Tyr-Phe-Gly -His-Thr-Asn-Tyr-Ile-Tyr-Ser -Ile-Ser-Val-Phe-Pro -Asn-Ser-Lys-Asp-Phe-Val-Thr-Thr (SEQ ID NO: 10)

Glu-Gln-Gly-Leu-Met-Leu -Thr-Gly-Ser-Ala-Asp-Lys-Thr-Ile -Lys-Leu-Trp-Lys-Ala-Gly-Arg-Cys-Glu-Arg-Thr-Phe (SEQ ID NO: 11);

and

Phe-Leu-Gly-His-Glu-Asp-Cys-Val-Arg-Gly-Leu-Ala-Ile -Leu-Ser-Glu-Thr-Glu-Phe-Leu-Ser-Cys-Ala-Asn-Asp-Ala (SEQ ID NO: 12).

4. The method of claim 2, wherein said fragment of phospholipase A₂ activating polypeptide is from about six to about thirty amino acids in length and wherein said fragment comprises at least one of amino acids 131, 132, 192, 193, 260, 261, 262, 263, 264, 265, 266, 267, 268, 269, 270, 271, 272, 273, 274, 275, 276, 277, 278, 279 and 280 of said phospholipase A₂ activating polypeptide, and the remainder of the amino acids of said fragment are selected from the amino acid sequence of phospholipase A₂ activating polypeptide contiguous with said at least one amino acid in the direction of the amino terminus of phospholipase A₂ activating polypeptide, the carboxy terminus of phospholipase A₂ activating polypeptide, or both.

5. The method of claim 1 wherein at least one half of the amino acids of said fragment are selected, in sequence, from amino acids 260, 261, 262, 263, 264, 265, 266, 267, 268, 269, 270, 271, 272, 273, 274, 275, 276, 277, 278, 279 and 280 of said phospholipase A₂ activating polypeptide.

6. The method of claim 1, wherein said phospholipase A₂ activating polypeptide is that of SEQ ID NO: 1.

7. The method of claim 3, wherein said fragment is that of SEQ ID No: 2.

8. The method of claim 3, wherein said fragment is that of SEQ ID No: 3.

9. The method of claim 3, wherein said fragment is that of SEQ ID No: 4.

10. The method of claim 3, wherein said fragment is that of SEQ ID No: 5.

11. The method of claim 3, wherein said fragment is that of SEQ ID No: 6.

12. The method of claim 3, wherein said fragment is that of SEQ ID No: 7.

13. The method of claim 3, wherein said fragment is that of SEQ ID No: 8.

14. The method of claim 3, wherein said fragment is that of SEQ ID No: 9.

15. The method of claim 3, wherein said fragment is that of SEQ ID No: 10.

16. The method of claim 3, wherein said fragment is that of SEQ ID No: 11.

17. The method of claim 3, wherein said fragment is that of SEQ ID No: 12.

18. The method of claim 2, wherein said fragment is that of SEQ ID No: 13.

* * * * *